United States Patent
Wu et al.

(10) Patent No.: US 8,298,990 B2
(45) Date of Patent: Oct. 30, 2012

(54) STABILIZED AGRICULTURAL OIL DISPERSIONS

(75) Inventors: Dan Wu, Carmel, IN (US); Kuide Qin, Westfield, IN (US); Franklin N. Keeney, Carmel, IN (US); Mei Li, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/093,879

(22) Filed: Apr. 26, 2011

(65) Prior Publication Data

US 2011/0275516 A1 Nov. 10, 2011

Related U.S. Application Data

(60) Provisional application No. 61/327,750, filed on Apr. 26, 2010.

(51) Int. Cl.
*A01N 25/00* (2006.01)
(52) U.S. Cl. ................................................. 504/116.1
(58) Field of Classification Search ....................... None
See application file for complete search history.

(56) References Cited

U.S. PATENT DOCUMENTS

| | | | | |
|---|---|---|---|---|
| 5,599,768 A | * | 2/1997 | Hermansky | 504/211 |
| 6,743,756 B2 | | 6/2004 | Harris, Jr. | |

FOREIGN PATENT DOCUMENTS

| | | | |
|---|---|---|---|
| WO | WO 02/36566 | * | 5/2002 |
| WO | WO02/36566 A1 | | 5/2002 |

* cited by examiner

*Primary Examiner* — Alton Pryor
(74) *Attorney, Agent, or Firm* — Robert Chang

(57) ABSTRACT

Agrochemical oil dispersions are stabilized to particle sedimentation by use of a combination of a clay or silica type rheology modifier and a polymer or oligomer capable of hydrogen bonding.

19 Claims, No Drawings

STABILIZED AGRICULTURAL OIL DISPERSIONS

CROSS REFERENCE TO RELATED APPLICATIONS

This application claims the benefit of U.S. Provisional Patent Application Ser. No. 61/327,950 filed Apr. 26, 2010.

FIELD OF THE INVENTION

This invention concerns agrochemical oil dispersions stabilized against particle sedimentation by the use of a combination of a clay or silica type rheology modifier and a polymer or oligomer capable of hydrogen bonding.

BACKGROUND OF THE INVENTION

Agricultural formulation products must be physically and chemically stable for a specified period of time in order to have commercial utility. There are many causes of formulation instabilities, such as active ingredient instability, phase separations and environmental factors (temperature, humidity/moisture, etc.). In today's agrochemical market, it is becoming increasingly common to develop new formulations containing multiple active ingredients and their required solvents, safeners, and/or adjuvants, etc., in order to achieve the optimal spectrum, efficacy and delivery efficiency, which consequently makes formulation stability more and more challenging. Therefore, technologies that can effectively isolate, hinder or eliminate adverse reactions or interactions between incompatible ingredients are often critical for a successful product.

An agrochemical active ingredient, such as a herbicide, insecticide or fungicide or a herbicide safener, can rarely be used in its originally manufactured form. Agrochemical products generally consist of two parts, the active ingredient and the co-formulants or inert ingredients combined together in a formulation. The combination of these two parts into the final product is conducted with two primary goals in mind: (1) maintaining the stability of the product during storage and (2) providing an easy and effective way to use the product upon dilution in a carrier such as water or oil for spray application to an area to be treated.

Agrochemical formulations are generally designed based on customer needs and the physiochemical properties of the active ingredient(s), for example, the solubility of the active ingredient in water and other non-aqueous solvents. There are two major categories of formulations, solid formulations and liquid formulations. Liquid formulations are generally preferred by customers due to their ease of handling in measuring, pumping, diluting and spraying operations.

Oil dispersions (OD) are one type of liquid formulation and are defined as stable suspensions of active ingredients in a water-immiscible fluid which may contain other dissolved active ingredients and is intended for dilution with water before use. Oil dispersion formulations have recently become more important in current formulation research. In addition to customer preferences for liquid formulations, oil dispersion formulations are very suitable for the following scenarios: (1) water sensitive active ingredients, e.g., sulfonylureas which may be susceptible to degradation by hydrolysis, 2) compatibility issues with active ingredient mixtures and 3) the need for build-in adjuvancy.

The basic components of an agricultural oil dispersion formulation are the solvent or oil phase and the dispersed solid phase. These basic components may include active ingredients, petroleum or naturally derived solvents, safeners, rheology modifiers, emulsifiers, dispersants and other co-formulants that help deliver the desired attributes of the product. Rheology modifiers provide physical stability to the formulation by increasing the viscosity of the liquid phase in order to prevent insoluble active ingredient particles from falling out of suspension and forming a layer at the bottom of the storage container. This phenomenon, known as sedimentation, can result in difficulties in the delivery and use of the product if the sediment layer of particles forms a hard pack that is difficult to disperse and re-suspend. A related physical instability of liquid formulations is syneresis. Syneresis in an oil dispersion formulation is generally measured as the amount of top-clearing due to phase separation.

There are a variety of materials, both natural and man-made, that have been used as rheology modifiers to stabilize oil dispersion formulations against sedimentation such as, for example, clays and organoclays, hydrophilic and hydrophobic silicas, hydrogenated castor oils and their derivatives, polyamides, oxidized waxes, associative thickeners, which form structures by themselves due to their limited solubility in solvents, and steric dispersants (e.g., comb polymers such as polyvinylpyrrolidinones or polyacrylates).

It is very common to combine one or more rheology modifiers in a single oil dispersion formulation to obtain the desired rheological properties and, at the same time, minimize any adverse interactions that may occur between ingredients. The proper choice and amounts of oil dispersion rheology modifiers can enhance the thickening efficacy and application range of a particular formulation. Factors to consider in the selection of rheology modifiers in the design of a stable oil dispersion formulation are the type of solvent, the interactions with emulsifiers, the robustness in activation of the thickeners and the temperature sensitivity of the final system.

While there are rheology modifiers available for use in stabilizing agrochemical oil dispersion formulations against particle sedimentation, there is a constant need for new ways to stabilize these formulations owing to limitations with existing choices, incompatibilities with surfactants and active ingredients and the diversity in chemistry of new active ingredients and solvents being discovered and developed today. In addition, the increasing number of active ingredients included in a single formulation can present formulation challenges. These limitations may be overcome by finding new rheology modifiers or additives that act to improve the performance of existing rheology modifiers.

Certain man-made and naturally derived polymers may be used in combination with conventional rheology modifiers such as hydrophilic and hydrophobic silicas, colloidal silicon dioxides, clays, and organoclays to improve the stability of oil dispersion formulations against sedimentation such as those disclosed, for example, in U.S. Pat. No. 5,599,768 and U.S. Pat. No. 6,743,756. In these examples, protic solvents such as alcohols, glycols, water and the like are necessary additives or solvents that are integral to the thickening effect of the rheology system leading to inhibition of particle settling during product storage. However, protic solvents such as water or alcohols may at times be incompatible with some active ingredients and herbicide safeners present in oil dispersion formulations. In particular, in the presence of water some sulfonylurea herbicides have a tendency to hydrolyze via cleavage at the sulfonylurea bridge as described, for example, by J.-P. Carnbon and J. Bastide in, "Hydrolysis Kinetics of Thifensulfuron Methyl in Aqueous Buffer Solutions," J. Agric. Food Chem., 44, pg. 333-337 (1996). The herbicide safener cloquintocet mexyl is also very prone to hydrate formation upon exposure to water, as disclosed, for example, in WO 02/36566 A1, with subsequent Ostwald Ripening of the resulting hydrate crystals. Because of these and other active ingredient and co-formulant incompatibilities, there is a continued need for new rheology systems that stabilize oil dispersions to particle settling.

The present invention describes agricultural oil dispersion compositions of improved stability containing active ingredients and safeners that can at times be prone to chemical degradation by protic solvents or other active ingredients. It has been found that when polymers or oligomers capable of hydrogen bonding are used in combination with clay or silica type rheology modifiers, in the absence of protic solvents, they provide improved physical stability to oil dispersion formulations of agrochemical products. The present invention provides new compositions of stable oil dispersion formulations of agrochemical products that are suitable in controlling undesired vegetation, insects and plant diseases, the inventive composition consisting essentially of an organic solvent, a dispersed active ingredient, a clay or silica type rheology modifier, a polymer or oligomer capable of hydrogen bonding and at least one surfactant.

SUMMARY OF THE INVENTION

The present invention concerns a stable oil dispersion formulation which consists essentially of:
a) an organic solvent comprising, with respect to the total composition, from about 200 grams per liter (g/L) to about 999 g/L;
b) a polymer or oligomer capable of hydrogen bonding comprising, with respect to the total composition, from about 1 g/L to about 200 g/L;
c) at least one dispersed active ingredient comprising, with respect to the total composition, from about 1 g/L to about 700 g/L;
d) a clay or silica type rheology modifier comprising, with respect to the total composition, from about 1 g/L to about 200 g/L; and
e) at least one surfactant comprising, with respect to the total composition, from about 1 g/L to about 600 g/L.

Another aspect of the present invention concerns a method of using the stable oil dispersion formulation and optionally diluting it in an aqueous spray mixture for agricultural applications such as with an aqueous dispersed herbicide for weed management.

A further aspect of the present invention concerns the stable oil dispersion composition optionally containing a soluble active ingredient or an herbicide safener or mixtures thereof.

DETAILED DESCRIPTION OF THE INVENTION

The present invention provides new compositions of stable oil dispersion formulations of agrochemical products that are suitable for controlling undesired vegetation, insects and plant diseases, the inventive composition consisting essentially of an organic solvent, a dispersed active ingredient, a clay or silica type rheology modifier, a polymer or oligomer capable of hydrogen bonding and at least one surfactant.

A stable oil dispersion formulation is defined as one that remains suspended for a period of up to two years under normal storage conditions.

The organic solvent of the current invention includes one or more of a water immiscible, aprotic organic chemical and, optionally, a polar aprotic organic chemical. The water immiscible, aprotic organic chemical comprises at least 70% by weight of the total amount of the organic solvent. The polar aprotic organic chemical may comprise no more than 30% by weight of the total amount of the organic solvent.

The water immiscible, aprotic organic chemical generally has less than about 0.5 percent by weight solubility in water and may include, but is not limited to, one or more of petroleum distillates such as aromatic hydrocarbons derived from benzene, such as toluene, xylenes, other alkylated benzenes and the like, and naphthalene derivatives, aliphatic hydrocarbons such as hexane, octane, cyclohexane, and the like, mineral oils from the aliphatic or isoparaffinic series, and mixtures of aromatic and aliphatic hydrocarbons; halogenated aromatic or aliphatic hydrocarbons; vegetable, seed or animal oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like, and $C_1$-$C_6$ mono-esters derived from vegetable, seed or animal oils; $C_1$-$C_6$ dialkyl amides of $C_6$-$C_{20}$ saturated and unsaturated aliphatic carboxylic acids; $C_1$-$C_{12}$ esters of aromatic carboxylic acids and dicarboxylic acids and $C_1$-$C_{12}$ esters of aliphatic and cyclo-aliphatic carboxylic acids; $C_4$-$C_{12}$ polyesters of dihydric, trihydric, or other lower polyalcohols such as, propylene glycol dioleate, di-octyl succinate, di-butyl adipate, di-octyl phthalate and the like.

The polar aprotic organic chemical, also referred herein as the co-solvent, may include, but is not limited to, one or more of ethers like tetrahydrofuran and the like, alkylene glycol dialkyl ethers such as ethylene glycol diethyl ether and the like, amides such as dimethylacetamide or N-methylpyrrolidone and the like, ketones such as methyl ethyl ketone and the like, nitriles such as butyronitrile and the like, sulfoxides or sulfones such as dimethyl sulfoxide or sulfolane and the like, and alkylene carbonates such as propylene or butylene carbonate and the like. The co-solvent may serve to aid in the activation of clay or organoclay rheology modifiers by helping to fully disperse and activate the particles of the rheology modifier so they may form an optimal rheological structure and provide suitable thickening to the composition during storage. The co-solvent may also serve to modify the polarity of the organic solvent in order to facilitate the solubility of active ingredients or co-formulant ingredients.

The organic solvent of the present invention may comprise, with respect to the total composition, from about 200 g/L to 999 g/L, preferably from about 300 g/L to 950 g/L.

The polymer or oligomer capable of hydrogen bonding of the present invention may include one or more polymers or oligomers that may be selected from the classes of polyethers, polyalcohols, polyamines, polyphenols, polyacrylic acids, polyvinyl ethers, polyvinyl ketones, polyvinyl heterocyclic compounds, polycarboxylic acid vinyls, modified celluloses, polysaccharides and polyamino acids, and derivatives, copolymers and oligomers thereof.

Polyethers may include polyoxymethylene, polyacetal, polyethylene glycol, polybutylene glycol, polytetramethylene oxide, polyoxymethylene alkyl ethers, polyethylene glycol alkyl ethers, polyoxyethylene alkyphenyl ethers, polyethylene glycol fatty acid esters, polyoxyethylene castor oil, polyoxyethylene hardened castor oil, polyoxyethylene alkylamines, polyoxyethylene fatty acid amides, polyoxyethylene alkylphenylformamide condensates, polyethylene glycol dialkyl ethers, polyethylene glycol dilaurate, polyoxyethylene glycol dioleate, polyethylene glycol distearate, polyethylene glycol diacrylate, polyethylene glycol dimethacrylate, polyethylene glycol dibenzoate, polyethylene glycol diglycidyl ether, polyethylene glycol divinyl ether, polyethylene glycol-n-alkylsulfopropyl ethers, polyethylene glycol biphenyl ether methacrylate, polyethylene glycol bisaminopropylterminate, polyethylene glycol bis(carboxymethyl)ether, polyethylene glycol bisethylhexanoate, polypropylene glycol, polypropylene glycol monoalkyl ethers, polypropylene glycol dialkyl ethers, polypropylene glycol fatty acid esters, polypropylene glycol acrylate, polypropylene glycol diacrylate, polyethylene glycol dibenzoate, polyethylene glycol diglycidyl ether, polyethylene glycol-propylene glycol copolymers, polyethylene glycol-propylene glycol alkyl ether copolymers, polyether rubber, crown ethers and polymers substituted with crown ethers, and the like.

Polyalcohols may include polyvinyl alcohol and co-polymers with other polymers such as vinyl alcohol-vinyl pyrrolidone copolymers and the like. Polyamines may include polyethylene imine, poly(N-acetylethylene imine), poly(N-formylethylene imine), polyvinyl amine and poly(N,N-dimethyl-N',N',N'',N''-tetramethylene phosphoramide) and co-polymers with other polymers, and the like. Polyphenols may include polyvinyl phenol, polyphenol imine diethanol isophthalate and phenol-formaldehyde resins. Polyacrylic acids may include polyacrylic acid, polymethacrylic acid, polyitaconic acid and esters thereof such as poly(methyl acrylate) and poly(methyl methacrylate), polyacrylamide, poly(dimethylaminoethyl methacrylate), poly(hydroxyethyl acrylate), poly(N-hydroxyethylacrylamide), poly(N-iso-propylacrylamide), poly(glycidyl methacrylate), poly(methoxy-polyethylene glycol monomethacrylate) and poly(diethoxy-n-methylitaconate), and the like.

Polyvinyl ethers may include polyvinyl methyl ether, polyvinyl ethyl ether, polyvinyl-iso-butyl ether, polyvinyl acetal, polyvinyl butyral, polyvinyl formal and polyethoxy-ethoxy-ethoxy-vinyl ether, and the like. Polyvinyl ketones may include polyvinyl methyl ketone and polyvinyl phenyl ketone, and the like. Polyvinyl heterocyclic compounds may include polyvinyl pyrrolidone, polyvinyl pyridine, polyvinyl piperazine, polyvinyl imidazole, polyvinyl imidazoline, polyvinyl carbazole, polyvinyl adenine and polyvinyl cytosine, and the like. Polycarboxylic acid vinyls may include polyvinyl acetate, polyvinyl cinnamate and maleic anhydrate-vinyl acetate copolymers, and the like. Polysaccharides may include starch, guar, amylose, cycloamylose, amiropectin, cellulose, alginic acid, glycogen, chitin and hyaluronic acid, and the like. Polyamino acids include polyglycine, polyserine, polylysine, oxytocin and polyglutamic acid, and the like.

Preferred polymers or oligomers capable of hydrogen bonding include at least one of a polyethylene glycol or polypropylene glycol.

The polymer or oligomer capable of hydrogen bonding of the present invention may have a number average molecular weight range of from about 200 to about 2,000,000, preferably from about 200 to about 100,000. The polymer or oligomer capable of hydrogen bonding of the present invention may comprise, with respect to the total composition, from about 1 g/L to about 200 g/L, preferably from about 1 g/L to about 100 g/L.

The dispersed active ingredients of the present invention may include the agrochemical active ingredient classes of insecticides, herbicides and fungicides. Suitable active ingredients from these classes generally have less than about 10 g/L, preferably less than 1 g/L solubility in the organic solvent.

Suitable dispersed active ingredients of the present invention may include one or more herbicides from, but not limited to, the classes of sulfonamides, sulfonylureas, arylpyridine carboxylic acids, arylpyrimidine carboxylic acids, hydroxy-benzonitriles, anilides, imidazolinones, carbazones and derivatives thereof; also, the free acids, alkali metal salts or amine salts of the herbicide classes of benzoic acids, phenoxyalkanoic acids, pyridinecarboxylic acids and pyridyloxycarboxylic acids herbicides.

Herbicides which may be suitable for dispersion in the organic solvent of the present invention include, but are not limited to, triasulfuron, tribenuron, metasulfuron, thifensulfuron, flupyrsulfuron, iodosulfuron, rimsulfuron, nicosulfuron, cinosulfuron, bensulfuron, trifloxysulfuron, foramsulphuron, mesosulphuron, sulphosulphuron, tritosulphuron and derivatives, furthermore flumetsulam, metosulam, chloransulam, florasulam, diclosulam, penoxsulam, pyroxsulam and derivatives, diflufenican, also imazethabenz, imazethapyr, imazaquin, imazamox and derivatives, and flucarbazone, propoxycarbazone, amicarbazone and derivatives, and compounds of the following generic structures and their derivatives,

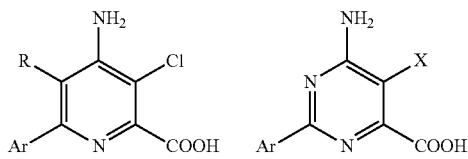

as disclosed in U.S. Pat. No. 7,314,849 B2, U.S. Pat. No. 7,300,907 B2 and U.S. Pat. No. 7,642,220 B2 wherein Ar is a polysubstituted phenyl group, R is H or halo and X is halo or alkoxy.

Additional herbicides which may be suitable for dispersion in the oil phase of the present invention include the free acids, alkali metal salts or amine salts of dicamba, 2,4-D, MCPA, 2,4-DB, aminopyralid, aminocyclopyrachlor, picloram, clopyralid, fluoroxypyr and triclopyr, and the alkali metal salts of bromoxynil and ioxynil. The amines may include primary, secondary, tertiary or quaternary alkylamines, alkanolamines, alkylalkanolamines or alkoxyalkanolamines wherein the alkyl and alkanol groups are saturated and contain $C_1$-$C_4$ alkyl groups individually. The alkali metals may include sodium and potassium.

For an oil dispersion formulation of the present invention the dispersible herbicides may comprise, with respect to the total composition, from about 1 g/L to about 700 g/L, preferably from about 1 g/L to about 500 g/L. It is commonly known that this concentrated formulation may be diluted from 1 to 2000 fold at point of use depending on the agricultural practices.

The clay or silica type rheology modifiers of the present invention may include one or more of a clay, an organoclay, a silica or a surface modified silica. To obtain the desired level of stability to particle sedimentation in a particular composition it is necessary to choose the rheology modifier and the polymer or oligomer capable of hydrogen bonding that provides the desired thickening effect. This can easily be determined by one of ordinary skill in the art. The clay type rheology modifiers may require a chemical activator, such as propylene carbonate, to help fully disperse and activate the mineral particles so they may form an optimal rheological structure and provide suitable thickening to the composition during storage. Preferred rheology modifiers include the organoclays such as Bentone, Bentone SD and Benathix Plus (all from Elementis Specialties, Inc.) and the fumed silicas such as Aerosil R974, Aerosil 200 and Aerosil 972 (all from Evonik Industries), and equivalent products thereof.

The clay or silica type rheology modifier of the present invention may comprise, with respect to the total composition, from about 1 g/L to about 200 g/L, preferably from about 1 g/L to about 100 g/L.

It is usually desirable to incorporate one or more surface-active agents commonly known as surfactants into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

The surfactant of the present invention may comprise, with respect to the total composition, from about 1 g/L to about 600 g/L, preferably from about 1 g/L to about 200 g/L.

In a general procedure for preparing the oil dispersion composition of the present invention, the organic solvent is charged into a vessel and the clay or silica type rheology modifier is added into the vessel with high shear mixing to allow complete wetting of the rheology modifier. The active ingredients, safener, dispersants, and emulsifier may then be added to the vessel under shearing conditions until the formation of a uniform oil dispersion is achieved. If an organoclay-type rheology modifier is being used, a chemical activator/co-solvent such as propylene carbonate may next be added to the vessel with high shear mixing to aid in the wetting and solvation of the organoclay thickener. The polymer or oligomer capable of hydrogen bonding may be introduced into the oil dispersion at a point where the desired thickening effect is achieved.

An example of an oil dispersion formulation of the present invention containing water sensitive active ingredients in which sedimentation of the dispersed active ingredients is retarded comprises:

a) an organic solvent comprising, with respect to the total composition, from about 200 g/L to about 950 g/L of Aromatic 150ND, and from about 10 g/L to about 200 g/L of propylene carbonate;
b) a herbicide safener comprising, with respect to the total composition, from about 10 g/L to about 500 g/L of cloquintocet mexyl;
c) a polymer or oligomer capable of hydrogen bonding comprising, with respect to the total composition, from about 1 g/L to about 200 g/L of Carbowax PEG 600;
d) a dispersed active ingredient comprising, with respect to the total composition, from about 1 g/L to about 200 g/L of pyroxsulam;
e) a dispersed active ingredient comprising, with respect to the total composition, from about 0.5 g/L to about 200 g/L of florasulam;
f) a soluble active ingredient comprising, with respect to the total composition, from about 10 g/L to about 500 g/L of fluoroxypyr methylheptyl ester;
g) an organoclay rheology modifier comprising, with respect to the total composition, from about 1 g/L to about 200 g/L of Benathix Plus;
h) a surfactant comprising, with respect to the total composition, from about 10 g/L to about 400 g/L of Tensiofix N9824 HF; and
i) optionally, other inert formulation ingredients.

Another aspect of the present invention concerns a method of using the stable oil dispersion formulation and optionally diluting it in an aqueous spray mixture for agricultural applications such as with an aqueous dispersed herbicide for weed management.

A further aspect of the present invention concerns the stable oil dispersion containing additional active ingredients or safeners that can be either dispersed or dissolved in the oil phase (organic solvent). These additional active ingredients and safeners may include the agrochemical active ingredient classes of insecticides, herbicides, fungicides and herbicide safeners.

Suitable additional active ingredients of the present invention that may be soluble in the oil phase include one or more herbicides, insecticides or fungicides, but are not limited to, esters of carboxylate, phosphate, or sulfate pesticides. These oil soluble active ingredients may include benzoic acid herbicides such as dicamba esters, phenoxyalkanoic acid herbicides such as 2,4-D, MCPA and 2,4-DB esters, aryloxyphenoxypropionic acid herbicides such as clodinafop, cyhalofop, fenoxaprop, fluazifop, haloxyfop and quizalofop esters, pyridinecarboxylic acid herbicides such as aminopyralid, picloram and clopyralid esters, pyrimidinecarboxylic acid herbicides such as aminocyclopyrachlor esters, pyridyloxyalkanoic acid herbicides such as fluoroxypyr and triclopyr esters, hydroxybenzonitrile herbicides such as bromoxynil and ioxynil esters, esters of the arylpyridine carboxylic acids and arylpyrimidine carboxylic acids of the following generic structures as disclosed in U.S. Pat. No. 7,314,849 B2, U.S. Pat. No. 7,300,907 B2 and U.S. Pat. No. 7,642,220 B2

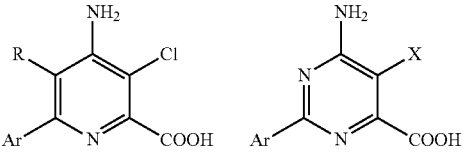

wherein Ar is a polysubstituted phenyl group, R is H or halo and X is halo or alkoxy, and insecticides such as chlorpyrifos and chlorpyrifos-methyl, and fungicides such as dinocap, meptyl dinocap, kresoxim-methyl, and the like. An especially suitable herbicide for dissolution in the oil phase is Compound A which has the following formula

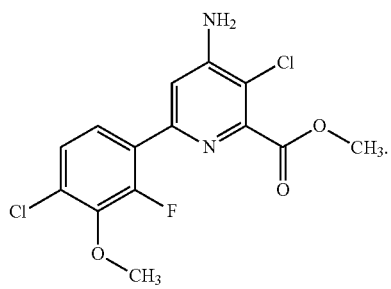

Additional ingredients of the present invention that may be soluble in or dispersed in the organic solvent may include one or more herbicide safeners. Suitable herbicide safeners of the present invention may include, but are not limited to, cloquintocet, benoxacor, cyometrinil, cyprosulfamide, dichlormid, dicyclonon, dietholate, fenchlorazole ethyl, fenclorim, flurazole, fluxofenim, furilazole, isoxadifen ethyl, mefenpyr diethyl, mephenate, naphthalic anhydride, oxabetrinil and derivatives and analogs thereof.

The additional active ingredients and herbicide safeners of the present invention may individually comprise, with respect to the total composition, from about 1 g/L to about 700 g/L, preferably from about 1 g/L to about 500 g/L.

Another aspect of the present invention concerns a method of preparing the oil dispersion of the present invention, the method consisting of:

a) preparing a pre-mix of the fully wetted and dispersed clay or silica type rheology additive in the solvent;

b) adding one or more of the active ingredient, safener, dispersant, and emulsifier to the mixture in a) under shearing conditions until a uniform oil dispersion is obtained;

c) adding the chemical activator to mixture b) with high shear mixing if an organoclay type rheology modifier is being used;

d) adding the polymer or oligomer capable of hydrogen bonding to mixture c) with mixing until a well mixed dispersion is obtained.

The most optimal method of preparing oil dispersions of the present invention can easily be determined by one of ordinary skill in the art.

The effective amount of the oil dispersion formulation of the present invention to be employed in a typical agricultural application often depends upon, for example, the type of plants, the stage of growth of the plant, severity of environmental conditions, the weeds, insects or fungal pathogens to be controlled and application conditions. Typically, a plant in need of protection from weeds or insects, or disease pathogen control or elimination, is contacted with an amount of the oil dispersion formulation diluted in a carrier such as water that will provide an amount from about 1 to about 40,000 ppm, preferably from about 10 to about 20,000 ppm of the active ingredient. It is commonly known that this concentrated formulation may be diluted from 1 to 2000 fold at point of use depending on the agricultural practices. The contacting may be in any effective manner. For example, any exposed part of the plant, e.g., leaves or stems may be sprayed with the active ingredient in mixture with a suitable amount of a diluent or carrier such as water.

The aforementioned compositions of the present invention may be applied to the plant foliage or the soil or area adjacent to the plant. Additionally, the compositions of the present invention may be mixed with or applied with any combination of agricultural active ingredients such as herbicides, insecticides, bacteriocides, nematocides, miticides, biocides, termiticides, rodenticides, molluscides, arthropodicides, fertilizers, growth regulators, and pheromones.

The composition of the present invention may optionally include one or more additional co-formulant ingredients such as antifoam agents, adjuvants, stabilizers, solvents, fragrants, sequestering agents, neutralizing agents, buffers, corrosion inhibitors, dyes, odorants and other commonly used ingredients.

The following examples illustrate the present invention.

Example 1

Preparation of Compositions of the Present Invention

The following general procedure describes the preparation of inventive compositions with the ingredients and the quantities listed in Table 1. The solvent Aromatic 150 ND (naphthalene depleted Aromatic 150) was charged into a vessel and the thickener Benathix Plus (Elementis Specialties) was added to the vessel and high shearing was applied to the system to allow complete wetting out of the rheological additive. Then the active ingredients, safener, dispersants, emulsifier and stabilizer were gradually added into the mixture under shearing conditions until the formation of a uniform dispersion. The chemical activator propylene carbonate was then added and high shearing was applied to allow the complete wetting and solvation/activation of the organoclay thickener. The resulting fully dispersed mixture was then treated with the polyethylene or polypropylene glycol and mixed well to provide the final sample.

TABLE 1

Ingredients Used to Prepare Oil Dispersions of the Present Invention

| Component | Role | Amount (g/L) |
|---|---|---|
| florasulam | active ingredient | 2.14 |
| fluroxypyr-meptyl | active ingredient | 123.2 |
| pyroxsulam | active ingredient | 12.8 |
| cloquintocet-mexyl | herbicide safener | 38.5 |
| Atlox 4912 | dispersant | 10 |
| Pluronic F108 | dispersant | 4 |
| Tensiofix N9824 HF | emulsifier | 80 |
| epoxidized soybean oil | stabilizer | 10 |
| Benathix Plus | organoclay suspension agent | 30 |
| polyethylene glycol or polypropylene glycol | polymer or oligomer additive | 20-50 |
| propylene carbonate | co-solvent/organoclay activator | 30 |
| Aromatic 150 ND | solvent | balance |

Example 2

Rheological Testing of Compositions of the Present Invention

The samples prepared as described in Example 1 above were evaluated rheologically to determine the effect of the added polymer or oligomer capable of hydrogen bonding on the formation and stability of the organoclay gel micro-structure that provides the thickening effect. A TA AR1000 rheometer was setup in a cone and plate geometry with a 60 mm diameter cone and 2° angles and was used to measure the rheological properties of the oil-dispersion formulations. Two testing steps, a stress sweep step and a frequency sweep step, were conducted with each sample. All data was collected at 25° C. and is summarized in Table 2. During the stress sweep step, the formulation is oscillated with increasing stress and the storage (G') and loss moduli (G") are determined. Both moduli initially are independent of stress, giving a plateau value known as the linear viscoelastic region (LVER). The length of the linear viscoelastic region shows how far the formulation can be deformed before the onset of gel micro-structure breakdown. From the measurement of the frequency sweep step, the degree of dispersion and inter-particle association can be determined. The frequency sweep test gives a good indication of how the product will behave during storage and application. For an oil dispersion system, a weak gel or network structure is a preferred system, where the storage moduli (G') is larger than the elastic moduli (G") at higher frequency. As shown in Table 2 for a control sample (sample A) containing all of the ingredients except the polymer or oligomer capable of hydrogen bonding, a smaller linear viscoelastic region (0.932 Pa) and a very weak gel network structure (G">G' at frequency 10 Hz) were measured indicating that this sample may not have good long term storage stability. Samples B-E, containing from 20-50 g/L of Carbowax PEG 600 (a polyethylene glycol) or Polyglycol P4000 (a polypropylene glycol), exhibited larger viscoelastic regions (1.218 to 3.842 Pa) and had storage moduli (G') larger than their elastic moduli (G") at higher frequency than did sample A as shown in Table 2. Samples B-E would therefore be expected to be more resistant to the vibrations and small movements experienced during storage than would sample A and would therefore be more resistant to particle sedimentation. The rheological measurements tabulated in Table 2 show there is a beneficial effect on sample rheology when the polymers or oligomers capable of hydrogen bonding were used in combination with the Benathix Plus organoclay to thicken the compositions and inhibit particle sedimentation as compared to sample A where the organoclay was used alone.

TABLE 2

Rheological Evaluation of Oil Dispersion Samples Containing Polymer or Oligomer Additives on the TA AR1000 Rheometer

| | | Rheological Measurement | |
|---|---|---|---|
| Sample | Polymer or Oligomer Additive* | Stress sweep step (linear viscoelastic region in Pa) | Frequency sweep step |
| A | no polymer added - control comparison sample | 0.932 | G" > G' at 10 Hz |
| B | 20 g/L Carbowax PEG 600 | 3.298 | G' > G" at 10 Hz |
| C | 50 g/L Carbowax PEG 600 | 3.842 | G' > G" at 10 Hz |
| D | 20 g/L Polyglycol P4000 | 1.218 | G' > G" at 10 Hz |
| E | 50 g/L Polyglycol P4000 | 1.472 | G' > G" at 10 Hz |

*Carbowax PEG 600 and Polyglycol P4000 are products of the Dow Chemical Company

A near infrared centrifugation technique was also used to estimate the long term stability of oil dispersion formulations A-E to particle sedimentation. A multi-sample analytical centrifuge-LUMiSizer® was used to simultaneously measure the intensity of transmitted light passed through a sample as a function of time to measure the degree of sedimentation. The analytical centrifuge LumiSizer allows one to speed-up the separation of oil dispersions by application of a centrifugal force (acceleration in the movement of particles compared to normal gravity) to the sample. The separation behavior of the individual samples can then be compared and analyzed in detail by tracing the variation in near infrared transmission through any part of the sample or by tracing the movement of any phase boundary.

Oil dispersion formulations A-E (Table 2) were analyzed for particle sedimentation under centrifugal force at 1,000 rpm for 100 minutes. The transmission of infrared light through the samples as a function of time was monitored and the integration profiles of each sample were measured. The percent integral light transmission after 1, 30 and 90 minutes of centrifugation of samples A-E are shown in Table 3. Oil dispersion sample A showed significant particle separation after centrifugation for 90 minutes (significant change in transmission indicating high potential for sedimentation), whereas samples B-E, which are based on compositions of the current invention, showed no significant separation. With the addition of Carbowax PEG 600 or Polyglycol P4000 to samples B-E, a strong effect between the rheological modifiers and the added polymers was realized indicating these formulations have better long term stability than sample A. These analytical centrifugation results (Table 3) show good agreement with the results obtained in the rheological measurements of Example 1 (Table 2), therefore, the combined results show that clay-based rheological modifiers when used with the polymers or oligomers capable of hydrogen bonding of the present invention can result in the preparation of oil dispersion formulations with improved stability to sedimentation.

TABLE 3

Near Infrared Analytical Centrifugation of Oil Dispersion Samples of the Present Invention

| | | % Near IR Integral Transmission After Centrifugation at 1000 rpm (24.9-26.5° C.) | | |
|---|---|---|---|---|
| Sample | Polymer or Oligomer Additive | 1 min. | 30 min. | 90 min. |
| A | no polymer added - control | 5.43 | 7.40 | 7.95 |
| B | 20 g/L Carbowax PEG 600 | 5.66 | 5.72 | 5.64 |
| C | 50 g/L Carbowax PEG 600 | 5.32 | 5.37 | 5.35 |
| D | 20 g/L Polyglycol P4000 | 5.21 | 5.31 | 5.29 |
| E | 50 g/L Polyglycol P4000 | 5.26 | 5.34 | 5.29 |

What is claimed:

1. An oil dispersion of improved stability consisting essentially of:
    a) an aprotic organic solvent comprising, with respect to the total composition, from about 200 g/L to about 999 g/L;
    b) a polymer or oligomer capable of hydrogen bonding comprising, with respect to the total composition, from about 1 g/L to about 200 g/L;
    c) a dispersed active ingredient comprising, with respect to the total composition, from about 1 g/L to about 700 g/L;
    d) a clay or silica rheology modifier comprising, with respect to the total composition, from about 1 g/L to about 200 g/L; and
    e) at least one surfactant comprising, with respect to the total composition, from about 1 g/L to about 600 g/L.

2. The composition of claim 1 wherein the polymer or oligomer capable of hydrogen bonding comprises at least one of a polyethylene glycol or polypropylene glycol.

3. The composition of claim 1 wherein the dispersed active ingredient comprises at least one herbicide selected from the classes of sulfonamides, sulfonylureas, arylpyridine carboxylic acids and esters thereof, arylpyrimidine carboxylic acids and salts, esters or amides thereof, hydroxybenzonitriles, anilides, imidazolinones, and carbazones.

4. The composition of claim 3 wherein the dispersed herbicide is at least one of triasulfuron, tribenuron, metasulfuron, thifensulfuron, flupyrsulfuron, iodosulfuron, rimsulfuron, nicosulfuron, cinosulfuron, bensulfuron, trifloxysulfuron, foramsulphuron, mesosulphuron, sulphosulphuron, tritosulphuron, flumetsulam, metosulam, chloransulam, florasulam, diclosulam, penoxsulam, pyroxsulam, diflufenican, imazethabenz, imazethapyr, imazaquin, imazamox, flucarbazone, propoxycarbazone, amicarbazone, and compounds of the following generic structures,

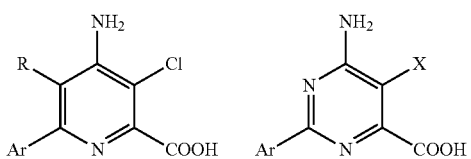

wherein Ar is a polysubstituted phenyl group, R is H or halo and X is halo or alkoxy.

5. The composition of claim 1 further comprising at least one of an additional insecticide, herbicide, fungicide or herbicide safener either dispersed or dissolved in the organic solvent.

6. The composition of claim 5 wherein the additional herbicide is fluoroxypyr-meptyl.

7. The composition of claim 5 wherein the additional herbicide is an arylpyridine carboxylic acid or ester of the formula

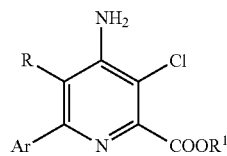

wherein Ar is a polysubstituted phenyl group, R is H or halogen and $R^1$ is H or $C_1$-$C_8$ alkyl.

8. The composition of claim 7 wherein the arylpyridine carboxylic acid or ester has the formula

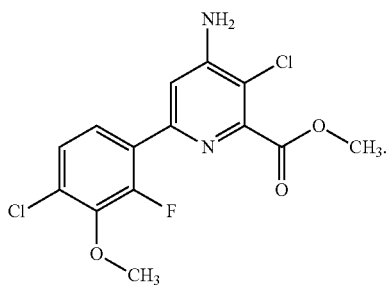

9. The composition of claim 5 wherein the herbicide safener is cloquintocet-mexyl.

10. The composition of claim 1 further comprising at least one of an antifoam agent, an adjuvant, a stabilizer, a fragrant, a sequestering agent, a neutralizing agent, a buffer, a corrosion inhibitor, a dye, an odorant and other commonly used inert ingredients.

11. The composition of claim 1 wherein the aprotic organic solvent comprises from about 300 g/L to about 950 g/L.

12. The composition of claim 1 wherein the polymer or oligomer capable of hydrogen bonding comprises from about 1 g/L to about 100 g/L.

13. The composition of claim 1 wherein the dispersed active ingredient comprises from about 1 g/L to about 500 g/L.

14. The composition of claim 1 wherein the clay or silica type rheology modifier comprises from about 1 g/L to about 100 g/L.

15. The composition of claim 1 wherein the surfactant comprises from about 1 g/L to about 200 g/L.

16. The composition of claim 1 wherein the clay or silica type rheology modifier comprises a clay or an organoclay.

17. The composition of claim 5 wherein the additional insecticide, herbicide, fungicide or herbicide safener comprises from about 1 g/L to about 700 g/L.

18. The composition of claim 17 wherein the additional insecticide, herbicide, fungicide or herbicide safener comprises from about 1 g/L to about 500 g/L.

19. The composition of claim 1 wherein the composition comprises:
   a) an organic solvent comprising, with respect to the total composition, from about 200 g/L to about 950 g/L of aromatic hydrocarbon, and from about 10 g/L to about 200 g/L of propylene carbonate;
   b) a herbicide safener comprising, with respect to the total composition, from about 10 g/L to about 500 g/L of cloquintocet mexyl;
   c) a polymer or oligomer capable of hydrogen bonding comprising, with respect to the total composition, from about 1 g/L to about 200 g/L of polyethylene glycol;
   d) a dispersed active ingredient comprising, with respect to the total composition, from about 1 g/L to about 200 g/L of pyroxsulam;
   e) a dispersed active ingredient comprising, with respect to the total composition, from about 0.5 g/L to about 200 g/L of florasulam;
   f) a soluble active ingredient comprising, with respect to the total composition, from about 10 g/L to about 500 g/L of fluoroxypyr methylheptyl ester;
   g) an organoclay rheology modifier at a concentration of from about 1 g/L to about 200 g/L with respect to the total composition;
   h) a surfactant at a concentration of from about 10 g/L to about 400 g/L with respect to the total composition; and
   i) optionally, other inert formulation ingredients.

* * * * *